(12) United States Patent
Gibson

(10) Patent No.: US 8,404,937 B2
(45) Date of Patent: Mar. 26, 2013

(54) SPEEDWAY LETTUCE VARIETY

(75) Inventor: George D. Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 290 days.

(21) Appl. No.: 12/882,050

(22) Filed: Sep. 14, 2010

(65) Prior Publication Data

US 2011/0083235 A1   Apr. 7, 2011

Related U.S. Application Data

(60) Provisional application No. 61/242,747, filed on Sep. 15, 2009.

(51) Int. Cl.
*A01H 5/00* (2006.01)
*A01H 5/10* (2006.01)
(52) U.S. Cl. .................... 800/305; 800/260; 435/410
(58) Field of Classification Search ................... None
See application file for complete search history.

(56) References Cited

U.S. PATENT DOCUMENTS 8,203,034 B2 * 6/2012 Waycott .................. 800/305

* cited by examiner

*Primary Examiner* — Eileen B O Hara
(74) *Attorney, Agent, or Firm* — Morrison & Foerster LLP

(57) ABSTRACT

A new lettuce variety designated Speedway is described. Speedway is an iceberg lettuce variety exhibiting stability and uniformity.

9 Claims, 1 Drawing Sheet

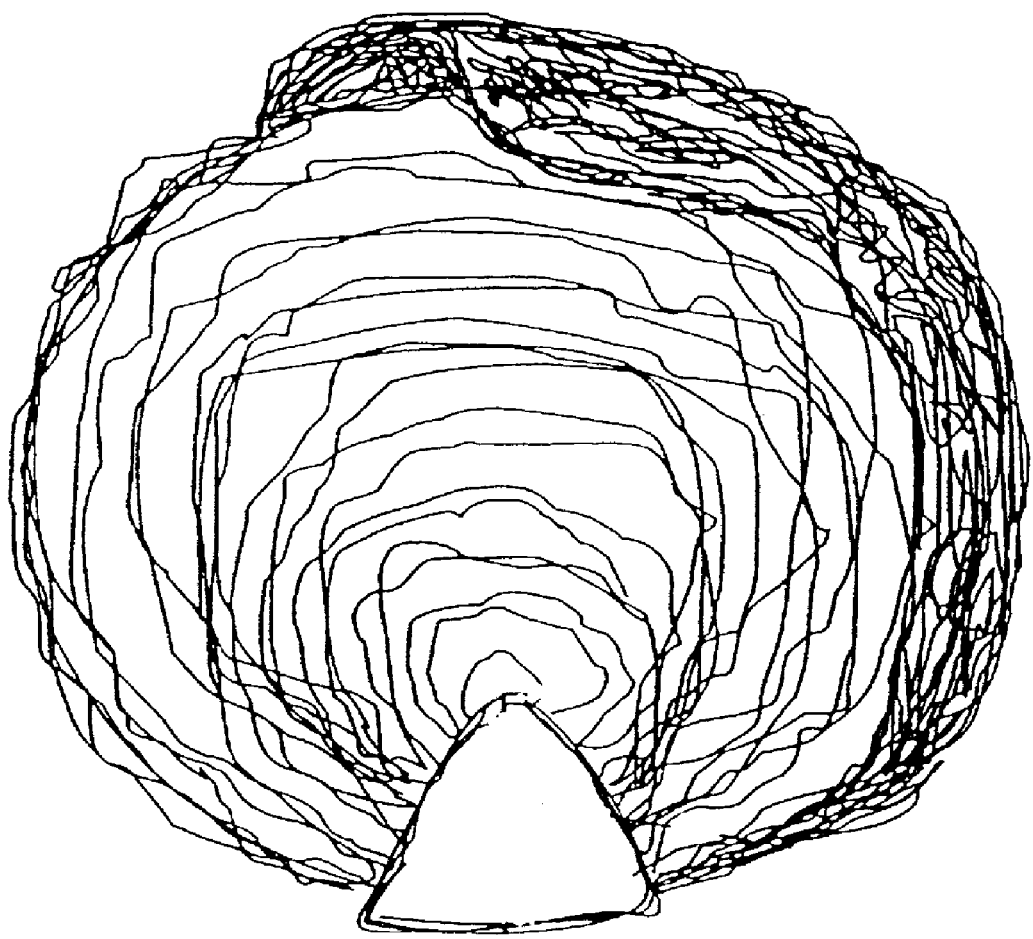

US 8,404,937 B2

SPEEDWAY LETTUCE VARIETY

RELATED APPLICATION

This application claims the benefit under 35 USC 119(e) of prior copending U.S. Provisional Patent Application No. 61/242,747, filed Sep. 15, 2009, the disclosure of which is hereby incorporated by reference in its entirety.

I. FIELD OF THE INVENTION

This invention relates to the field of plant breeding. In particular, this invention relates to a new lettuce, *Lactuca sativa*, variety, Speedway.

II. BACKGROUND OF THE INVENTION

Lettuce is an increasingly popular crop. Worldwide lettuce consumption continues to increase. As a result of this demand, there is a continued need for new lettuce varieties. In particular, there is a need for improved iceberg lettuce varieties that exhibit vigorous growth, increased weight and yield.

III. SUMMARY OF THE INVENTION

In order to meet these needs, the present invention is directed to an improved iceberg lettuce variety that exhibits vigorous growth, increased weight and yield. In particular, the present invention is directed to *Lactuca sativa* seed designated as Speedway having ATCC Accession Number PTA-11670. The present invention is further directed to a *Lactuca sativa* plant produced by growing Speedway lettuce seed having ATCC Accession Number PTA-11670. The present invention is further directed to a *Lactuca sativa* plant having all the physiological and morphological characteristics of a *Lactuca sativa* plant produced by growing Speedway lettuce seed having ATCC Accession Number PTA-11670. The present invention is further directed to an $F_1$ hybrid *Lactuca sativa* plant having Speedway as a parent wherein Speedway lettuce seed is grown from Speedway seed having ATCC Accession Number PTA-11670.

The present invention is further directed to pollen isolated from Speedway lettuce plants. The present invention is further directed to tissue culture of Speedway lettuce plants.

The present invention is further directed to a method of selecting lettuce comprising
 a) growing Speedway lettuce plants wherein the plants are grown from lettuce seed having ATCC Accession Number PTA-11670 and
 b) selecting a plant from step a).

The present invention is further directed to lettuce plants and seeds produced therefrom wherein the lettuce plant is isolated by the selection method of the invention.

The present invention is further directed to a method of breeding lettuce comprising crossing a lettuce plant with a plant grown from Speedway lettuce seed having ATCC Accession Number PTA-11670. The present invention is further directed to lettuce plants and seeds produced there from wherein the lettuce plant is isolated by the breeding method of the invention.

IV. BRIEF DESCRIPTION OF THE FIGURE

FIG. 1 The invention will be better understood by reference to FIG. 1 which shows a drawing of cross-section of an iceberg lettuce head showing head length, head diameter, core diameter, core length and a wrapper leaf.

V. BRIEF DESCRIPTION OF THE TABLES

The invention will be better understood by reference to the Tables in which;
 Table 1 shows trial data comparing Icon and Speedway iceberg lettuce varieties.
 Table 2 shows trial data comparing Icon and Speedway iceberg lettuce varieties.
 Table 3 shows trial data comparing Icon and Speedway iceberg lettuce varieties.

VI. DETAILED DESCRIPTION OF THE INVENTION

In order to more clearly understand the invention, the following definitions are provided:
 Iceberg Lettuce Iceberg lettuce, *Lactuca sativa* L. var. capitata L. is also known as 'crisp head' lettuce. Iceberg lettuce is a lettuce plant type that forms a firm, spherical head formed with tightly folded brittle textured foliage. Internal color ranges from white to yellow to light green. The wrapper leaves surrounding the head are wider than they are long. Leaf margins can vary by type, being entire, undulating, or frilled. Wrapper leaf color ranges from yellow green to dark green.
 Core Length Core length is the length of the internal lettuce stem. Core length is measured from the base of the cut head to the tip of the core.
 Core Diameter Core diameter is the diameter of the lettuce stem at the base of the cut head.
 Head Diameter Head diameter is the diameter of the vertically sliced lettuce plant head at its widest horizontal point, perpendicular to the stem.
 Head Length Head length is the diameter of the vertically sliced lettuce plant head as measured from the base of the cut stem to the cap leaf.
 Average Head Diameter Average head diameter is an average of the measured head diameter and head length of the lettuce head.
 Average Head Diameter: Core Length The ratio of the average head diameter to core length is indicative of the percentage of useable product produced by the lettuce plant.
 Frame Diameter The frame diameter is a measurement of the lettuce plant diameter at its widest point. The measurement of frame diameter is from the outer most wrapper leaf tip to outer most wrapper leaf tip.
 Head Weight Weight of the marketable lettuce plant, cut and trimmed to market specifications.
 Rogueing Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.
 Market Stage Market stage is the stage when a lettuce plant is ready for commercial lettuce harvest. In the case of an iceberg variety, the head is solid, and has reached an adequate size and weight.
 Taking into account these definitions, the present invention is directed to seeds of the lettuce variety Speedway, plants produced by growing Speedway seeds, plants selected from a collection of Speedway plants and seeds derived or produced therefrom; plants produced by crossed a lettuce plant with a Speedway lettuce plant and seeds derived or produced therefrom.

VII. ORIGIN AND BREEDING HISTORY OF THE VARIETY SPEEDWAY

Speedway is a Salinas type iceberg lettuce variety developed from a hand pollinated cross of the cultivars Viper and Pybas 251. The initial cross was made in a San Joaquin valley research and development seed production field year one. The F1 seed harvested was designated as #931511. Viper, a medium sized heavily textured vanguard type iceberg lettuce was selected as a source of improved texture, adaptability for the spring harvest period in the desert south west, and bolting and tip burn resistance. Pybas 251 was selected for its improved vigor, and Salinas type characteristics. By implementation of the pedigree selection breeding method we developed a sure heading, heavily textured Salinas type iceberg lettuce variety with excellent resistance to tip burn and bolting for spring harvest in the desert south west and Huron lettuce production regions.

Approximately 50 plants of the F1 seed were planted in a San Joaquin Valley research seed production field for seed increase in year two. The F2 seed was harvested in mass in August 1994, labeled 94067.

An F2 population of 94067 was planted in a research and development field trial in Yuma in year two. Individual F2 plants were selected at market maturity specifically for a Salinas type iceberg, with improved size, improved leaf texture, shorter cores and resistance to tip burn. The particular individual plant selection labeled 94067-1 was noted to demonstrate the desired Salinas type, improved leaf texture, was slower bolting, and did not show any signs of tip burn. The selected plants were removed from the trial, and allowed to fully mature in our green house facility. The F3 seed from the selections were harvested in the early spring of year three.

The F3 seed from the single plant was then planted in our research and development seed production crop in the San Joaquin Valley in year four. The line, 97Y166 was evaluated, and additional individual plants were selected. The individual plants that were selected demonstrated the desired Salinas type, improved leaf texture, were slower bolting, and did not show any signs of tip burn. These individual plants were flagged in the field, allowed to grow to full maturity, and the F4 seed from each was harvested individually.

The F4 lines from the individual plant selections were included in a research and development plot trial in the winter of year six in Yuma, Ariz. The F4 lines were evaluated at market maturity and additional individual plant selections were made based on the attributes described above. The selected plants were labeled and removed from the research plot trial and allowed to grow to full maturity in a greenhouse facility. The F5 seed from the individual plant selections was harvested.

The F5 lines from the individual plant selections were included in a research and development plot trial in the spring of year eight in the Salinas valley to screen for type, texture, days to bolting and tip burn. The F5 lines were evaluated at market maturity and individual plant selections were made for improved vigor, improved texture and improved size. The selected plants were labeled and allowed to continue to grow in the field ten days past market maturity, where they were again evaluated. The individual plants that were slowest to bolt and free of tip burn were selected, removed from the research plot trial, and allowed to grow to full maturity in a greenhouse facility. The F6 seed from the individual plant selections was harvested.

The F6 selections were then increased in a research and development seed production nursery in the San Joaquin valley. The F6 lines were evaluated and selectively rogued for uniformity in size, type and maturity. The F7 seed from each line was mass harvested. The F6 lines were evaluated in trials in the spring of year ten and year eleven in the desert south west lettuce production region, and item number PSJV02262 was noted to best demonstrate the combined attributes. PSJV02262 was clearly a uniform Salinas type iceberg lettuce variety, with improved size and vigor, improved texture, slower bolting and had a higher resistance to tip burn than the commercial standards and sister lines.

PSJV02262 was again increased in a year eleven research and development seed production block in the San Joaquin valley were it was noted to be uniform, stable and free of variants. The F8 seed was harvested in mass in the late summer of year eleven, identified as PSJV042742. PSJV042742 was trialed in multiple times and locations throughout the desert south west for the spring harvest slot in the year eleven/year twelve growing season, where it continued to out perform commercial standard varieties and other research lines in development. Based on these results, the item was advanced and designated as PX 1544 in year thirteen.

PX 1544 was increased in year thirteen research and development seed production block in the San Joaquin valley. The variety was evaluated and noted to be uniform, stable and free of variants. The F9 seed was harvested in mass in the late summer of year thirteen. Additional trialing of F9 seed for spring harvest in the desert south west was conducted in year thirteen, fourteen and fifteen.

PX 1544 was named 'Speedway' in the Fall of year fifteen and a commercial seed increase was grown in year sixteen.

As evaluated in seed production and field trials the F8, the F9, and the F10 seed from the variety Speedway has been uniform and stable with out variants.

A. Variety Description Information

| | |
|---|---|
| Plant Type: | Iceberg |
| Seed: | |
| Seed Color: | White |
| Light Dormancy: | No |
| Heat Dormancy: | Yes |
| Cotyledons: | |
| Shape of Cotyledons: | Intermediate |
| Shape of Fourth Leaf: | Intermediate |
| Length/Width Index of Fourth Leaf: | 36 |
| Apical Margin: | Moderately Dentate |
| Basal Margin: | Finley Dentate |
| Undulation: | Slight |
| Green Color: | Dark |
| Anthocyanin: | Absent |
| Distribution: | None |
| Rolling: | Absent |
| Cupping: | Uncupped |
| Reflexing: | Lateral Margins |
| Mature Leaves: | |
| Margin: | |
| Incision Depth (Deepest penetration of the margin): | Moderate |
| Indentation (Finest Division of the Margin): | Crenate |
| Undulation of the Apical Margin: | Absent |
| Green Color: | Dark |

-continued

| Anthocyanin | |
|---|---|
| Distribution: | None |
| Size: | Large |
| Glossiness: | Moderate |
| Blistering: | Moderate |
| Leaf Thickness: | Thick |
| Trichomes: | Absent |

B. Comparison to Most Similar Variety

| Characteristic | Speedway | Icon* |
|---|---|---|
| Spread of Frame Leaves | 50 cm | 49 cm |
| Head Diameter (market trimmed with single cup leaf) | 16 cm | 16 cm |
| Head Shape | Spherical | Spherical |
| Head Size Class | large | Large |
| Head Count per Carton | 24 | 24 |
| Head Weight | 986 grams | 864 grams |
| Head Firmness | Firm | Firm |
| Butt | | |
| Shape | Rounded | Rounded |
| Midrib | Moderately Raised | Moderately Raised |
| Core (Stem of Market-trimmed Head) | | |
| Diameter at the base of the Head | 38 mm | 36 mm |
| Ratio of Head Diameter/Core Diameter | 4.2 | 4.4 |
| Core Height from base of Head to Apex | 30 mm | 41 mm |
| Number of Days from First Water | 61 | 60 |
| Date to Seed Stalk Emergence (Summer condition) | | |
| Bolting Class | Medium | Medium |
| Height of Mature Seed Stalk | 112 cm | 109 cm |
| Spread of Bolter Plant | 40 cm | 38 cm |
| Bolter Leaves | Curved | Curved |
| Margin | Dentate | Dentate |
| Color | Medium Green | Medium Green |
| Bolter Habit | | |
| Terminal Inflorescence | Present | Present |
| Lateral Shoots (above head) | Present | Present |
| Basal Side Shoots | Absent | Absent |
| Adaptation Regions | Desert South West | Desert South West |

C. Growing Season

| Season | Speedway | Icon* |
|---|---|---|
| Spring area | Not Adapted | Not Adapted |
| Summer area | Not Adapted | Not Adapted |
| Fall area | Not Adapted | Salinas Valley |
| Winter area: | Desert South West | Desert South West |

D. Diseases and Stress Reactions

| Disease or Stress Virus | Speedway | Icon* |
|---|---|---|
| Big Vein: | Susceptible | Susceptible |
| Lettuce Mosaic: | Resistant | Resistant |

E. Fungi/Bacteria

| Fungal/Bacterial | Speedway | Icon* |
|---|---|---|
| Corky Root Rot (*Pythium* Root Rot): | Susceptible | Susceptible |
| Downy Mildew (Races I, IIA, III): | Susceptible | Susceptible |
| Powdery Mildew: | Susceptible | Susceptible |
| *Sclerotinia* Rot: | Susceptible | Susceptible |
| Bacterial Soft Rot (*Pseudomonas* spp. & others): Not tested | | |
| *Botrytis* (Gray Mold): | Susceptible | Susceptible |
| Other: Corky Root Rot (*Rhizomonas suberifaciens*): | Susceptible | Susceptible |

F. Insects

| Insects | Speedway | Icon* |
|---|---|---|
| Cabbage Loopers: | Susceptible | Susceptible |
| Root Aphids: | Susceptible | Susceptible |
| Green Peach Aphid: | Susceptible | Susceptible |

G. Physiological/Stress

| Stress | Speedway | Icon* |
|---|---|---|
| Tipburn | Resistant | Moderately Susceptible |
| Heat | Moderately Susceptible | Moderately Susceptible |
| Drought | Susceptible | Susceptible |
| Cold | Resistant | Resistant |
| Salt | Susceptible | Susceptible |

H. Post Harvest

| Characteristic | Speedway | Icon* |
|---|---|---|
| Pink Rib | Moderately Susceptible | Moderately Susceptible |
| Russet Spotting | Moderately Susceptible | Moderately Susceptible |
| Rusty Brown Discoloration | Moderately Susceptible | Moderately Susceptible |
| Internal Rib Necrosis (Blackheart, Gray Rib, Gray Streak) | Moderately Susceptible | Moderately Susceptible |

*Icon is available from Progeny Advance Genetics, Salinas, California.

Breeding and Selection

The present invention is further directed to the use of Speedway lettuce in breeding and selection of new varieties.

A. Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture, and size for fall plantings in Yuma Ariz., and Huron Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen may be performed by procedures well known in the art of lettuce breeding.

In addition to manual removal of anther tubes, A modified method of misting to wash the pollen off prior to fertilization may be used to assure crossing or hybridization. About 60-90 min past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen are washed off with enough pressure to dislodge the pollen grains, but not enough to damage the style. Excess water is dried off with clean paper towels. About 30 min later the styles should spring back up and the two lobes of the stigma are visibly open in a "V" shape. Pollen from another variety or donor parent are then introduced by gently rubbing the stigma and style of the donor parent to the maternal parent. Tags with the pertinent information on date and pedigree are then secured to the flowers.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the F2 generations when expected segregation patterns for the genetic character of interest can be followed. This latter situation mandates a lengthy wait to determine if hybrids are produced. Two useful references teaching the methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908.

B. Selection

In addition to crossing, selection may be used to isolate lettuce new lettuce lines. One or more lettuce seeds are planted, the plants are grown and single plant selections are made of plants with desired characteristics. Such characteristics may include improved head and frame size, deeper or darker green leaf color, etc. Seed from the single plant selections are harvested; separated from seeds of the other plants in the field and re-planted. The plants from the selected seed are monitored to determine if they exhibit the desired characteristics from the originally selected line. Selection work is continued over multiple generations to increase the uniformity and size of new line.

VIII. DEPOSIT INFORMATION

Applicants have made available to the public without restriction a deposit of at least 2500 seeds of lettuce variety Speedway with the American Type Culture Collection (ATCC), 10801 University Boulevard, Manassas, Va. 20110 with a deposit on Feb. 8, 2011, which has been assigned ATCC number PTA-11670.

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

IX. EXAMPLES

Example 1

General Trialing Method

I. Set Up
1. Parental lines and competing varieties are identified.
2. Primary slots are identified.
3. Necessary accession lines are located and purchased/received from seed dealers or growers.
4. All varieties are assigned a number to maintain integrity and anonymity.
5. Trials are set up in with all necessary varieties. Variety arrangement for trial is diagramed.

II. Planting
1. Commercial plantings are located by contacting commercial growers during the planting slot recommended for the variety.
2. A field is located during commercial planting, and the necessary rows and area is marked off.
3. Varieties are planted according to a diagram in 100 ft. ranges.
4. All varieties are planted in same manner to mimic the planting of the commercial variety as closely as possible.
5. A trial map is drawn diagramming the trial, the trial location in the field and directions to the field.

III. Maintenance
1. All varieties are treated identically. Plants are watered, fertilized, and treated to control pests in the same manner as the commercial field.
2. The trial is thinned to separate the plants for optimum growth.

Example 2

Comparative Analysis

Following the procedures of Example 1, Speedway iceberg lettuce was compared to its most similar variety. The data are presented in Tables 1-3. Table 1 shows trial data comparing Icon and Speedway iceberg lettuce varieties. Table 2 shows trial data comparing Icon and Speedway iceberg lettuce varieties. Table 3 shows trial data comparing Icon and Speedway iceberg lettuce varieties.

Speedway is a new and distinct variety of iceberg lettuce that most closely resembles the commercial variety Icon. Speedway is a Salinas type iceberg lettuce variety adapted to the spring harvest of the desert south west and Huron lettuce production regions of California and Arizona. Speedway is large heading and large framed, widely adapted variety, with improved heading characteristics, and improved resistance to tip burn and bolting.

Speedway is more widely adapted than Icon. Similar to Icon, Speedway is adapted to the spring harvest in the desert south west production region. Speedway is also adapted to the spring harvest of the Huron Calif. production region, where as Icon is not. When planted in Huron, Icon has a tendency to form puffy and open plants, where as Speedway consistently forms uniform, dense and solid heads. This increased adaptability can also be evident in the desert south west production, depending on the temperature and growing conditions. On warm years Icon has an increased tendency to form open and puffy heads. Whereas under conditions associated with warm or cold seasons, Speedway is consistently sure heading, and forms uniform and solid heads.

Speedway is distinguished from Icon by the following characteristics as represented in Tables 1-3.

Speedway has a significantly shorter core length than Icon.

Speedway is less susceptible to tip burn than Icon.

This data is represented in Tables 1, 2 and 3 and are statistically significant at the 95% confidence level, exhibiting a range of means for core length from 25.27 to 33.40 mm for Speedway and from 38.26 to 47.73 mm for Icon, incidence of tip burn from 3.3 to 10% for Speedway and ranging from 36.6 to 50% for Icon, with tip burn severity ranging from an index level of 0.06 to 0.14 for Speedway and from an index of 0.66 to 0.85 for Icon using the 0.95 probability of generating confidence intervals that contains the means.

TABLE 1

Evaluation of Speedway and the most similar cultivar Icon for core elongation measured to the nearest 5 mm.

| | Trial No. | | | | | | | |
|---|---|---|---|---|---|---|---|---|
| | 1 | | 2 | | 3 | | 4 | |
| | Location | | | | | | | |
| | Yuma, Az | | Yuma, Az | | Huron, CA | | Huron, CA | |
| | Core Length (mm) | | Core Length (mm) | | Core Length (mm) | | Core Length (mm) | |
| Plant | Speedway | Icon | Speedway | Icon | Speedway | Icon | Speedway | Icon |
| 1 | 35.0 | 35.0 | 40.0 | 45.0 | 35.0 | 50.0 | 35.0 | 50.0 |
| 2 | 30.0 | 35.0 | 40.0 | 45.0 | 35.0 | 50.0 | 35.0 | 50.0 |
| 3 | 30.0 | 40.0 | 45.0 | 50.0 | 30.0 | 40.0 | 35.0 | 45.0 |
| 4 | 35.0 | 40.0 | 40.0 | 50.0 | 35.0 | 50.0 | 30.0 | 45.0 |
| 5 | 20.0 | 35.0 | 40.0 | 50.0 | 35.0 | 55.0 | 30.0 | 45.0 |
| 6 | 20.0 | 40.0 | 40.0 | 50.0 | 30.0 | 40.0 | 35.0 | 40.0 |
| 7 | 25.0 | 40.0 | 35.0 | 45.0 | 35.0 | 50.0 | 40.0 | 40.0 |
| 8 | 25.0 | 30.0 | 30.0 | 45.0 | 35.0 | 55.0 | 40.0 | 35.0 |
| 9 | 20.0 | 30.0 | 35.0 | 55.0 | 35.0 | 45.0 | 35.0 | 35.0 |
| 10 | 20.0 | 25.0 | 30.0 | 55.0 | 30.0 | 55.0 | 40.0 | 50.0 |
| 11 | 35.0 | 35.0 | 30.0 | 55.0 | 30.0 | 45.0 | 35.0 | 50.0 |
| 12 | 35.0 | 35.0 | 30.0 | 50.0 | 35.0 | 45.0 | 40.0 | 50.0 |
| 13 | 35.0 | 35.0 | 30.0 | 55.0 | 30.0 | 55.0 | 40.0 | 55.0 |
| 14 | 30.0 | 40.0 | 25.0 | 50.0 | 35.0 | 55.0 | 35.0 | 55.0 |
| 15 | 25.0 | 45.0 | 35.0 | 35.0 | 30.0 | 50.0 | 35.0 | 55.0 |
| 16 | 25.0 | 50.0 | 30.0 | 40.0 | 25.0 | 45.0 | 35.0 | 35.0 |
| 17 | 20.0 | 50.0 | 25.0 | 40.0 | 35.0 | 45.0 | 30.0 | 35.0 |
| 18 | 20.0 | 45.0 | 25.0 | 40.0 | 25.0 | 40.0 | 30.0 | 30.0 |
| 19 | 20.0 | 45.0 | 20.0 | 45.0 | 25.0 | 40.0 | 35.0 | 35.0 |
| 20 | 20.0 | 45.0 | 25.0 | 45.0 | 35.0 | 55.0 | 30.0 | 45.0 |
| 21 | 25.0 | 40.0 | 20.0 | 35.0 | 20.0 | 40.0 | 25.0 | 50.0 |
| 22 | 30.0 | 40.0 | 20.0 | 50.0 | 35.0 | 45.0 | 20.0 | 50.0 |
| 23 | 30.0 | 40.0 | 20.0 | 55.0 | 20.0 | 45.0 | 25.0 | 35.0 |
| 24 | 25.0 | 40.0 | 25.0 | 40.0 | 35.0 | 50.0 | 20.0 | 35.0 |
| 25 | 20.0 | 25.0 | 35.0 | 55.0 | 35.0 | 40.0 | 35.0 | 35.0 |
| 26 | 20.0 | 35.0 | 30.0 | 35.0 | 20.0 | 45.0 | 35.0 | 30.0 |
| 27 | 25.0 | 35.0 | 20.0 | 50.0 | 20.0 | 50.0 | 30.0 | 35.0 |
| 28 | 20.0 | 30.0 | 25.0 | 55.0 | 20.0 | 50.0 | 40.0 | 35.0 |
| 29 | 20.0 | 45.0 | 20.0 | 50.0 | 25.0 | 50.0 | 35.0 | 30.0 |
| 30 | 20.0 | 45.0 | 25.0 | 45.0 | 25.0 | 50.0 | 35.0 | 35.0 |
| Average | 25.3 | 38.3 | 29.7 | 47.2 | 29.8 | 47.7 | 33.3 | 41.7 |
| Stan dev | 5.71E+00 | 6.48E+00 | 7.42E+00 | 6.39E+00 | 5.80E+00 | 5.21E+00 | 5.47E+00 | 8.24E+00 |
| T test | 2.47E−03 | | 6.82E−14 | | 3.76E−18 | | 2.20E−05 | |
| Probability % | 99.8 | | 100.0000 | | 100.0000 | | 99.9978 | |
| % Difference | −33.9 | | −37.1 | | −37.4 | | −20.0 | |
| Confidence Int | 0.0654 | 0.0742 | 0.0849 | 0.0732 | 0.0664 | 0.0596 | 0.0626 | 0.0943 |
| Range of Var min* | 25.27 | 38.26 | 29.58 | 47.09 | 29.77 | 47.61 | 33.27 | 41.57 |
| Range of Var max* | 25.40 | 38.41 | 29.75 | 47.24 | 29.90 | 47.73 | 33.40 | 41.76 |

*Range of variation among means of statistically significant differences at the 95% level using the confidence interval [C] = mean +/− {SDXSE}

TABLE 2

Evaluation of Speedway and most similar variety Icon for presence of tip burn

| | Trial No. | | | | | | | |
|---|---|---|---|---|---|---|---|---|
| | 1 | | 2 | | 3 | | 4 | |
| | Location | | | | | | | |
| | Yuma, Az | | Yuma, Az | | Huron, CA | | Huron, CA | |
| | Tip Burn Incidence | | Tip Burn Incidence | | Tip Burn Incidence | | Tip Burn Incidence | |
| Plant | Speedway | Icon | Speedway | Icon | Speedway | Icon | Speedway | Icon |
| 1 | 0.0 | 1.0 | 0.0 | 1.0 | 0.0 | 1.0 | 0.0 | 1.0 |
| 2 | 0.0 | 0.0 | 0.0 | 1.0 | 0.0 | 0.0 | 0.0 | 1.0 |
| 3 | 0.0 | 0.0 | 0.0 | 1.0 | 0.0 | 0.0 | 0.0 | 0.0 |
| 4 | 0.0 | 0.0 | 0.0 | 1.0 | 1.0 | 0.0 | 0.0 | 0.0 |
| 5 | 0.0 | 1.0 | 0.0 | 1.0 | 0.0 | 1.0 | 0.0 | 0.0 |

TABLE 2-continued

Evaluation of Speedway and most similar variety Icon for presence of tip burn

| | Trial No. | | | | | | | |
|---|---|---|---|---|---|---|---|---|
| | 1 | | 2 | | 3 | | 4 | |
| | Location | | | | | | | |
| | Yuma, Az Tip Burn Incidence | | Yuma, Az Tip Burn Incidence | | Huron, CA Tip Burn Incidence | | Huron, CA Tip Burn Incidence | |
| Plant | Speedway | Icon | Speedway | Icon | Speedway | Icon | Speedway | Icon |
| 6 | 0.0 | 0.0 | 0.0 | 1.0 | 0.0 | 0.0 | 0.0 | 1.0 |
| 7 | 1.0 | 0.0 | 0.0 | 0.0 | 0.0 | 1.0 | 0.0 | 0.0 |
| 8 | 0.0 | 1.0 | 0.0 | 0.0 | 0.0 | 1.0 | 1.0 | 0.0 |
| 9 | 0.0 | 0.0 | 0.0 | 1.0 | 0.0 | 1.0 | 1.0 | 0.0 |
| 10 | 0.0 | 0.0 | 0.0 | 1.0 | 0.0 | 0.0 | 0.0 | 1.0 |
| 11 | 1.0 | 0.0 | 0.0 | 1.0 | 0.0 | 0.0 | 0.0 | 1.0 |
| 12 | 0.0 | 1.0 | 0.0 | 1.0 | 0.0 | 0.0 | 0.0 | 0.0 |
| 13 | 0.0 | 1.0 | 0.0 | 1.0 | 0.0 | 1.0 | 0.0 | 0.0 |
| 14 | 0.0 | 1.0 | 0.0 | 1.0 | 0.0 | 1.0 | 0.0 | 1.0 |
| 15 | 0.0 | 1.0 | 0.0 | 0.0 | 0.0 | 0.0 | 0.0 | 0.0 |
| 16 | 0.0 | 1.0 | 0.0 | 0.0 | 0.0 | 0.0 | 0.0 | 1.0 |
| 17 | 0.0 | 0.0 | 0.0 | 0.0 | 0.0 | 1.0 | 0.0 | 0.0 |
| 18 | 0.0 | 0.0 | 0.0 | 0.0 | 0.0 | 1.0 | 0.0 | 1.0 |
| 19 | 0.0 | 0.0 | 0.0 | 1.0 | 0.0 | 0.0 | 0.0 | 0.0 |
| 20 | 0.0 | 1.0 | 0.0 | 0.0 | 0.0 | 1.0 | 0.0 | 1.0 |
| 21 | 0.0 | 1.0 | 0.0 | 0.0 | 0.0 | 0.0 | 0.0 | 0.0 |
| 22 | 0.0 | 1.0 | 0.0 | 0.0 | 0.0 | 0.0 | 0.0 | 0.0 |
| 23 | 0.0 | 1.0 | 0.0 | 0.0 | 0.0 | 0.0 | 0.0 | 1.0 |
| 24 | 0.0 | 1.0 | 1.0 | 1.0 | 0.0 | 0.0 | 0.0 | 0.0 |
| 25 | 0.0 | 1.0 | 0.0 | 1.0 | 0.0 | 1.0 | 1.0 | 0.0 |
| 26 | 0.0 | 0.0 | 0.0 | 0.0 | 0.0 | 0.0 | 0.0 | 0.0 |
| 27 | 0.0 | 0.0 | 0.0 | 0.0 | 0.0 | 0.0 | 0.0 | 0.0 |
| 28 | 0.0 | 0.0 | 0.0 | 0.0 | 0.0 | 0.0 | 0.0 | 0.0 |
| 29 | 0.0 | 0.0 | 0.0 | 0.0 | 0.0 | 1.0 | 0.0 | 0.0 |
| 30 | 0.0 | 0.0 | 0.0 | 0.0 | 0.0 | 0.0 | 0.0 | 1.0 |
| Total infected | 2.0 | 14.0 | 1.0 | 15.0 | 1.0 | 12.0 | 3.0 | 11.0 |
| Stan dev | 2.54E−01 | 5.07E−01 | 1.83E−01 | 5.09E−01 | 1.83E−01 | 4.98E−01 | 3.05E−01 | 4.90E−01 |
| T test | 2.86E−04 | | 1.48E−05 | | 3.67E−04 | | 1.42E−02 | |
| Probability % | 99.97 | | 100.00 | | 99.96 | | 98.58 | |
| % Difference | 85.7 | | 93.3 | | 91.7 | | 72.7 | |
| Confidence Int | 0.0029 | 0.0058 | 0.0021 | 0.0058 | 0.0021 | 0.0057 | 0.0035 | 0.0056 |
| Range of Var min* | 2.00 | 13.99 | 1.00 | 14.99 | 1.00 | 11.99 | 3.00 | 10.99 |
| Range of Var max* | 2.00 | 14.01 | 1.00 | 15.01 | 1.00 | 12.01 | 3.00 | 11.01 |

*Range of variation among means of statistically significant differences at the 95% level using the confidence interval [C] = mean +/− {SDXSE}
Tip burn incidence is rated as absent or present. If tip burn is absent in a head, a 0 is recorded. If tip burn is present in a head then a 1 is recorded.

TABLE 3

Evaluation of Speedway and most similar variety Icon for severity of tip burn

| | Trial No. | | | | | | | |
|---|---|---|---|---|---|---|---|---|
| | 1 | | 2 | | 3 | | 4 | |
| | Location | | | | | | | |
| | Yuma, Az Tip burn severity | | Yuma, Az Tip burn severity | | Huron, CA Tip burn severity | | Huron, CA Tip burn severity | |
| Plant | Speedway | Icon | Speedway | Icon | Speedway | Icon | Speedway | Icon |
| 1 | 0.0 | 2.0 | 0.0 | 3.0 | 0.0 | 1.0 | 0.0 | 2.0 |
| 2 | 0.0 | 0.0 | 0.0 | 2.0 | 0.0 | 0.0 | 0.0 | 2.0 |
| 3 | 0.0 | 0.0 | 0.0 | 2.0 | 0.0 | 0.0 | 0.0 | 0.0 |
| 4 | 0.0 | 0.0 | 0.0 | 1.0 | 2.0 | 0.0 | 0.0 | 0.0 |
| 5 | 0.0 | 3.0 | 0.0 | 1.0 | 0.0 | 3.0 | 0.0 | 0.0 |
| 6 | 0.0 | 0.0 | 0.0 | 2.0 | 0.0 | 0.0 | 0.0 | 3.0 |
| 7 | 2.0 | 0.0 | 0.0 | 0.0 | 0.0 | 3.0 | 0.0 | 0.0 |
| 8 | 0.0 | 1.0 | 0.0 | 0.0 | 0.0 | 2.0 | 2.0 | 0.0 |
| 9 | 0.0 | 0.0 | 0.0 | 1.0 | 0.0 | 1.0 | 1.0 | 0.0 |
| 10 | 0.0 | 0.0 | 0.0 | 2.0 | 0.0 | 0.0 | 0.0 | 1.0 |
| 11 | 2.0 | 0.0 | 0.0 | 1.0 | 0.0 | 0.0 | 0.0 | 1.0 |

TABLE 3-continued

Evaluation of Speedway and most similar variety Icon for severity of tip burn

| | Trial No. | | | | | | | |
|---|---|---|---|---|---|---|---|---|
| | 1 | | 2 | | 3 | | 4 | |
| | Location | | | | | | | |
| | Yuma, Az Tip burn severity | | Yuma, Az Tip burn severity | | Huron, CA Tip burn severity | | Huron, CA Tip burn severity | |
| Plant | Speedway | Icon | Speedway | Icon | Speedway | Icon | Speedway | Icon |
| 12 | 0.0 | 2.0 | 0.0 | 1.0 | 0.0 | 0.0 | 0.0 | 0.0 |
| 13 | 0.0 | 2.0 | 0.0 | 2.0 | 0.0 | 2.0 | 0.0 | 0.0 |
| 14 | 0.0 | 2.0 | 0.0 | 1.0 | 0.0 | 2.0 | 0.0 | 3.0 |
| 15 | 0.0 | 1.0 | 0.0 | 0.0 | 0.0 | 0.0 | 0.0 | 0.0 |
| 16 | 0.0 | 3.0 | 0.0 | 0.0 | 0.0 | 0.0 | 0.0 | 1.0 |
| 17 | 0.0 | 0.0 | 0.0 | 0.0 | 0.0 | 1.0 | 0.0 | 0.0 |
| 18 | 0.0 | 0.0 | 0.0 | 0.0 | 0.0 | 1.0 | 0.0 | 2.0 |
| 19 | 0.0 | 0.0 | 0.0 | 2.0 | 0.0 | 0.0 | 0.0 | 0.0 |
| 20 | 0.0 | 2.0 | 0.0 | 0.0 | 0.0 | 1.0 | 0.0 | 2.0 |
| 21 | 0.0 | 2.0 | 0.0 | 0.0 | 0.0 | 0.0 | 0.0 | 0.0 |
| 22 | 0.0 | 1.0 | 0.0 | 0.0 | 0.0 | 0.0 | 0.0 | 0.0 |
| 23 | 0.0 | 2.0 | 0.0 | 0.0 | 0.0 | 0.0 | 0.0 | 1.0 |
| 24 | 0.0 | 1.0 | 2.0 | 3.0 | 0.0 | 0.0 | 0.0 | 0.0 |
| 25 | 0.0 | 1.0 | 0.0 | 1.0 | 0.0 | 2.0 | 1.0 | 0.0 |
| 26 | 0.0 | 0.0 | 0.0 | 0.0 | 0.0 | 0.0 | 0.0 | 0.0 |
| 27 | 0.0 | 0.0 | 0.0 | 0.0 | 0.0 | 0.0 | 0.0 | 0.0 |
| 28 | 0.0 | 0.0 | 0.0 | 0.0 | 0.0 | 0.0 | 0.0 | 0.0 |
| 29 | 0.0 | 0.0 | 0.0 | 0.0 | 0.0 | 2.0 | 0.0 | 0.0 |
| 30 | 0.0 | 0.0 | 0.0 | 0.0 | 0.0 | 0.0 | 0.0 | 2.0 |
| Average | 0.1 | 0.8 | 0.1 | 0.8 | 0.1 | 0.7 | 0.1 | 0.7 |
| Stan dev | 5.07E−01 | 1.02E+00 | 3.65E−01 | 9.86E−01 | 3.65E−01 | 9.88E−01 | 4.34E−01 | 9.94E−01 |
| T test | 1.36E−03 | | 1.84E−04 | | 1.69E−03 | | 9.25E−03 | |
| Probability % | 99.86 | | 99.98 | | 99.83 | | 99.07 | |
| % Difference | 84.0 | | 92.0 | | 90.5 | | 80.0 | |
| Confidence Int | 0.0058 | 0.0117 | 0.0042 | 0.0113 | 0.0042 | 0.0113 | 0.0050 | 0.0114 |
| Range of Var min* | 0.13 | 0.82 | 0.06 | 0.82 | 0.06 | 0.69 | 0.13 | 0.66 |
| Range of Var max* | 0.14 | 0.85 | 0.07 | 0.84 | 0.07 | 0.71 | 0.14 | 0.68 |

*Range of variation among means of statistically significant differences at the 95% level using the confidence interval [C] = mean +/− {SDXSE}
Tip burn severity is rated on a scale of 1-5. 1 being slight decay and 5 being most severe decay.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

I claim:

1. *Lactuca sativa* seed designated as Speedway having ATCC Accession Number PTA-11670.

2. A *Lactuca sativa* plant produced by growing the seed of claim 1.

3. A *Lactuca sativa* plant having all the physiological and morphological characteristics of the *Lactuca sativa* plant of claim 2.

4. A $F_1$ hybrid *Lactuca sativa* plant having Speedway as a parent where Speedway is grown from the seed of claim 1.

5. Pollen of the plant of claim 2.

6. Pollen of the plant of claim 3.

7. Tissue culture of the plant of claim 2.

8. Tissue culture of the plant of claim 3.

9. A method of selecting lettuce, comprising
   a) growing more than one plant from the seed of claim 1; and
   b) selecting a plant from step a).

* * * * *